United States Patent
Egan et al.

(10) Patent No.: US 8,101,909 B2
(45) Date of Patent: Jan. 24, 2012

(54) TIME-OF-FLIGHT MASS SPECTROMETRY OF SURFACES

(75) Inventors: Thomas F. Egan, Houston, TX (US); J. Albert Schultz, Houston, TX (US); Steven R. Ulrich, Houston, TX (US); Kelley L. Waters, Houston, TX (US)

(73) Assignee: Ionwerks, Inc., Houston, TX (US)

( * ) Notice: Subject to any disclaimer, the term of this patent is extended or adjusted under 35 U.S.C. 154(b) by 323 days.

(21) Appl. No.: 12/360,011

(22) Filed: Jan. 26, 2009

(65) Prior Publication Data

US 2009/0189072 A1    Jul. 30, 2009

Related U.S. Application Data

(60) Provisional application No. 61/023,750, filed on Jan. 25, 2008.

(51) Int. Cl.
*H01J 49/40* (2006.01)
(52) U.S. Cl. ......... 250/287; 250/281; 250/282; 250/288
(58) Field of Classification Search .......... 250/281, 250/282, 283, 285, 286, 287, 288, 309
See application file for complete search history.

(56) References Cited

U.S. PATENT DOCUMENTS

| | | | |
|---|---|---|---|
| 5,032,724 A | | 7/1991 | Gerlach et al. |
| 5,068,535 A | * | 11/1991 | Rabalais .................. 850/16 |
| 5,087,815 A | | 2/1992 | Schultz et al. |
| 5,650,616 A | * | 7/1997 | Iketaki ...................... 250/288 |
| 6,291,820 B1 | * | 9/2001 | Hamza et al. ............. 250/282 |
| 6,294,790 B1 | * | 9/2001 | Weinberger ............... 250/397 |
| 6,633,034 B1 | * | 10/2003 | Crewe ......................... 850/9 |
| 6,670,624 B1 | | 12/2003 | Adams et al. |
| 2005/0127289 A1 | | 6/2005 | Fuhrer et al. |
| 2007/0085040 A1 | | 4/2007 | Reilly et al. |
| 2008/0111069 A1 | * | 5/2008 | Notte ........................ 250/282 |

OTHER PUBLICATIONS

International Preliminary Examination Report issued Jul. 27, 2010, during the prosecution of International Application No. PCT/US09/32038.
International Search Report issued Mar. 10, 2009, during the prosecution of International Application No. PCT/US09/32038.
Written Opinion issued Mar. 10, 2009, during the prosecution of International Application No. PCT/US09/32038.

* cited by examiner

*Primary Examiner* — Robert Kim
*Assistant Examiner* — Nicole Ippolito Rausch
(74) *Attorney, Agent, or Firm* — Fulbright & Jaworski L.L.P.

(57) ABSTRACT

The present invent provides a particle detector for counting and measuring the flight time of secondary electrons and scattered ions and neutrals and to correlate coincidences between these and backscattered ions/and neutrals while maintaining a continuous unpulsed microfocused primary ion beam for impinging a surface. Intensities of the primary particle scattering and secondary particle emissions are correlated with the position of impact of the focused beam onto a materials surface so that a spatially resolved surface elemental and electronic structural mapping is obtained by scanning the focused beam across the surface.

8 Claims, 11 Drawing Sheets

TIME-OF-FLIGHT MASS SPECTROMETRY OF SURFACES

CROSS-REFERENCE TO RELATED APPLICATIONS

This application claims benefit under 35 U.S.C. 119(e) to U.S. Provisional Application Ser. No. 61/023,750, filed on Jan. 25, 2008, which is incorporated by reference herein in its entirety.

TECHNICAL FIELD

The present invention generally relates to the fields of mass spectrometry and in particular the area of elemental surface analysis and imaging by mass spectrometry. Specifically, the invention concerns a method and apparatus for counting and measuring the flight time of secondary electrons, scattered ions and/or neutrals and for correlating coincidences between these and backscattered ions and/or neutrals while maintaining a continuous unpulsed microfocused primary ion beam for impinging a surface.

BACKGROUND OF THE INVENTION

Ion beams have been used as probes in TOF (Time-of-Flight) mass spectroscopy of surfaces of material for years (Hammond et al., 1995). Imaging and elemental analysis by energy analysis of the backscattered ions and backscattered neutrals and forward recoiled elemental ions and neutrals created during the collisions between incident ions and surfaces can yield information on both surface structure and composition. Scanning Focused Ion Beams (FIB) and recording the backscatter intensity (backscatter ions, secondary electrons, secondary ions sputtered from the surface) have been used to image semiconductor and biological surfaces and ion mill samples under investigation.

Measuring the backscattered ions/neutrals, the electrons generated when an ion beam strikes the surface of a material has been used extensively for elemental and structural analysis of the surface for the last 25 years. The co-axial impact collision ion scattering spectrometry (CAICISS) (Katayama et al., 1988 and Aono et al., 1992) technique was developed by measuring energy losses of backscattering Helium atoms and Helium ions when a nanosecond pulsed Helium ion beam impinges a surface. The energy of the backscattered Helium is determined by measuring the time of flight from the sample to the detector. The time of flight from the sample to the detector is relative to the time at which the Helium ion beam is initially pulsed. Since the mass of Helium is known and the length from the ion source to the sample and the sample to the detector are well defined by geometry, the energy loss of each Helium atom arriving at the detector can be computed. The energy will be high (fast time of flight) when the Helium backscatters from a heavy element and low when it strikes a light element (slow time of flight). It is important to note when using CAICISS most ions neutralize as they approach the surface and remain neutralized as the ions backscatter from the surface. Because the velocity of Helium at a few hundred to a few thousand eV of kinetic energy is still large enough, the neutral helium will be detected with near unit efficiency when they impinge a channel plate detector. Thus most of the Helium which backscatters from the surface into an angle subtended by the detector can be detected There are some limits to the elemental mass specificity of this technique. For example, light elements, such as Oxygen, are detected poorly by Helium backscatter relative to heavier elements, such as Zinc. Thus the technique may be used in conjunction with one or more detectors placed in the forward scattering direction so that the energy of light recoiled surface elements can be determined.

Another example and application of CAICISS is to monitor film growth. In such applications, elements such as Lanthanum (La) and Strontium (Sr) are difficult to resolve due to their similar masses which result in nearly equal Helium backscatter flight times. Depending on the azimuthal scattering angle, the signal intensities can vary significantly. The variation in signal intensity depends on scattering from heavy species like Lanthanum (La) or Strontium (Sr) compared to the lighter material like Manganese. Also, the variation in signal intensity depends on the surface structure (where each element is shadowing and blocking its nearest neighbor at certain angles).

The physical scale of these instruments is another drawback. The beamline and backscattering detector are over a meter in length. The actual flight path for the backscattered ions/neutrals is about 500 millimeters (mm), this path length is necessary to obtain an acceptable spectra when the pulse of Helium is tens of nanoseconds. Also, because of this geometry, the angle subtended by a 50 millimeters diameter detector, the detector is very small (less than 1 degree half angle).

When scanning a microfocused energetic primary particle beam (electron, ion, photon), spatially resolved microprobe images of the surface are routinely obtained. The microprobe images are most often obtained by measuring and recording the variation of the secondary electron yield as the particle beam is scanned from one microfocused point on the surface to the next. Also, the images may be obtained by other contrast mechanisms such as by measuring the intensity, the energy and/or the mass of secondary ejected particles using an ionizing radiation such as photon irradiation. The secondary ejected particles include but are not limited to photons, backscattered primary particles, secondary ions directly created and sputtered by the incoming primary particle beam, or secondary ions created by photoionizing sputtered neutral elements or molecules. The present invention provides a detector for correlating coincident particle emissions with spatial imaging by a laser or particle beam microprobe.

BRIEF SUMMARY OF THE INVENTION

The present invent provides a particle detector for counting and measuring the flight time of secondary electrons and scattered ions and neutrals and to correlate coincidences between these and backscattered ions/and neutrals while maintaining a continuous unpulsed microfocused primary ion beam for impinging a surface. Intensities of the primary particle scattering and secondary particle emissions are correlated with the position of impact of the focused beam onto a materials surface so that a spatially resolved surface elemental and electronic structural mapping is obtained by scanning the focused beam across the surface.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

It is readily apparent to the skilled artisan that various embodiments and modifications can be made to the invention disclosed in this Application without departing from the scope and spirit of the invention.

As used herein "a" or "an" means one or more than one unless expressly stated to the contrary or otherwise clear from the context. For example, reference to "a species" means one species or more than one species.

Figure 1:
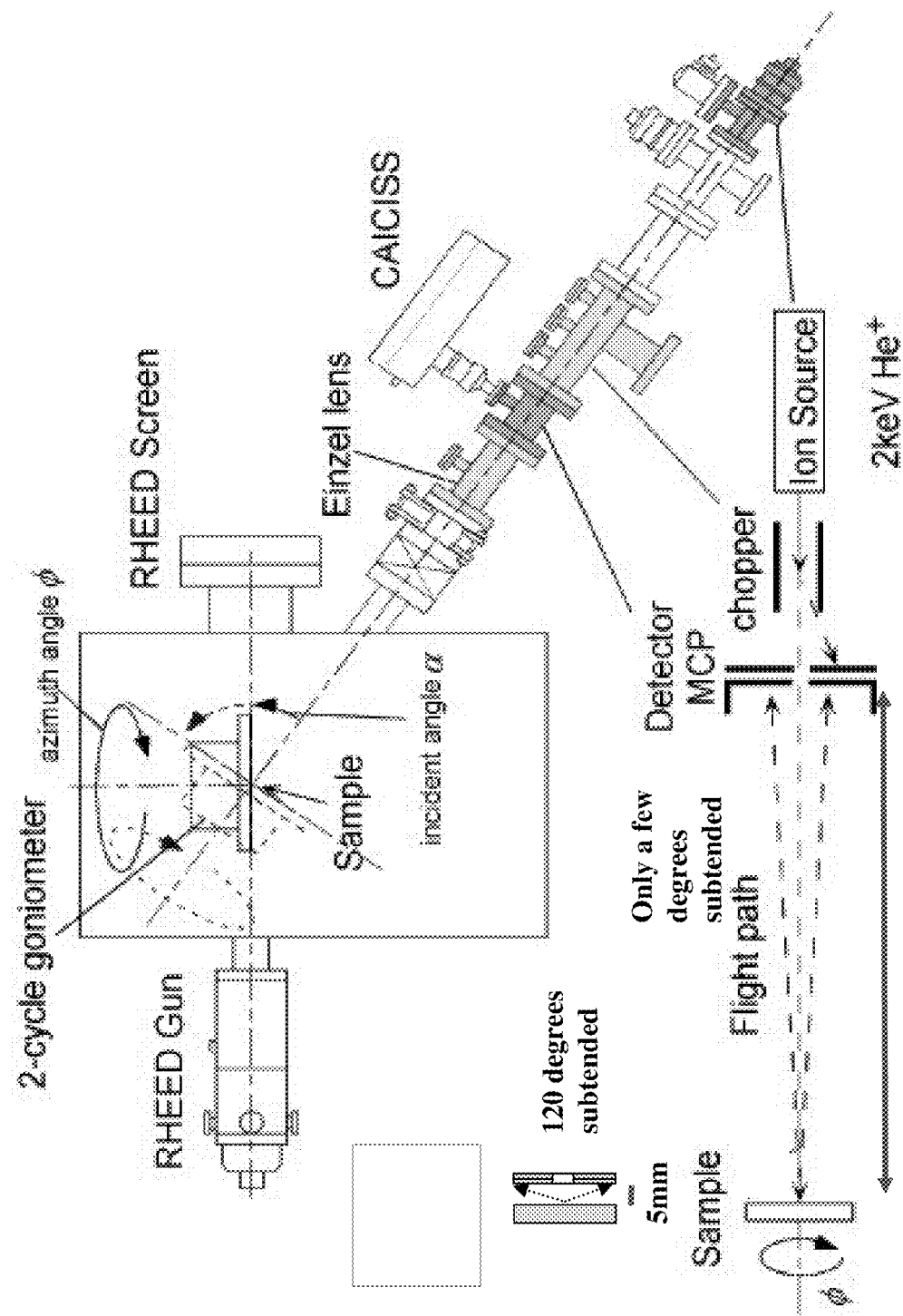
FIG. 1 shows an example of a CAICISS instrument.

An example of CAICISS instrument can be found in FIG. 1. In the CAICISS technique, the elemental composition of a surface is determined by pulsing a mono-energetic Helium (He) ion beam so that a packet of ions hits the surface all within a few nanoseconds. Since the Helium will lose a specific amount of energy when it backscatters from a particular element, it is then possible to collect the information regarding the elemental composition of a surface. The elemental composition is determined by evaluating the loss peaks in a Helium time-of-flight spectrum in which the loss peaks correlate with the Helium arrival times at backscatter detector. If the Helium strikes a heavier element, then the Helium loses very little energy and comes back to the detector quickly. However, if the Helium strikes a lighter element then more energy is lost by the Helium during the collision and the Helium backscatters with a slower velocity.

Typically, a monoenergetic continuous He beam of a few KeV is generated in the ion source. The "chopper" electronically deflects this continuous Helium ion beam across a slit so that only a small number of ions is allowed to pass through the slit/detector within a few nanoseconds and then the ions travel on to the sample. The flight time of the Helium from the slit/detector to the sample and the flight time when the Helium packet strikes the sample can be calculated accurately due to the known geometry of these paths. When the Helium packet strikes the sample, most of the Helium ions are neutralized. Some of the resulting neutral Helium atoms will backscatter by binary or ternary collisions with surface atoms and return to the detector. In comparing the collision between Helium and a heavy surface atom and the collision between Helium and a light surface atom, the Helium loses less energy when colliding with a heavy surface atom. Therefore, the time of flight of the Helium to the detector will be faster when Helium collides with a heavy atom and the time of flight of Helium to the detector will be slower when Helium collides with a light element. Even in the case of collisions with light elements, the backscattered Helium species have sufficient velocity to be recorded by the detector even when scattering from the light elements. Thus repeated pulsing of the beam and collecting the times of flight of each of the backscattered Helium species will result in a spectrum which measures the presence of different elements on the surface (see FIG. 2 and FIG. 3). Note the large scale of the instrument and the small angle subtended by the detector (as shown in the schematic located under the instrumental cross-section).

Figure 2:
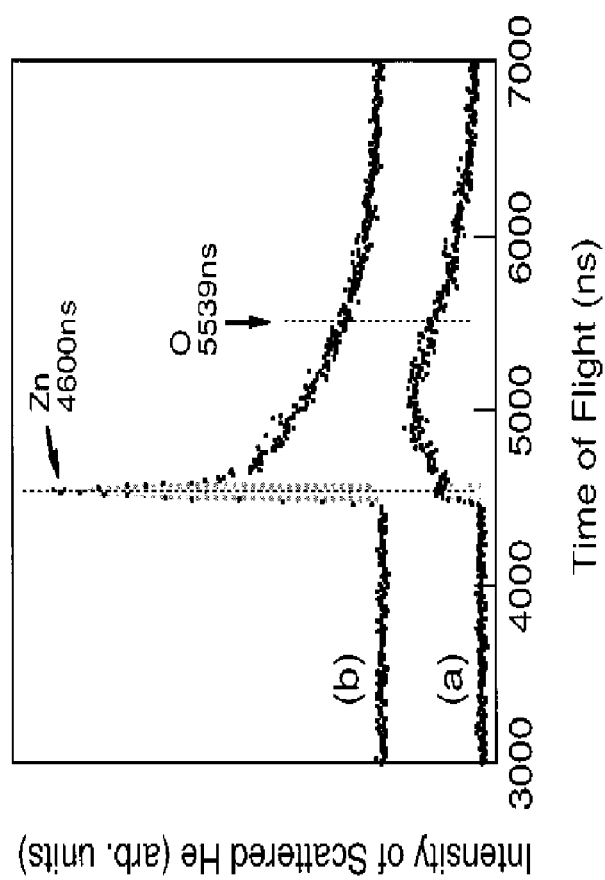
FIG. 2 shows a Time-Of-Flight spectra of the surface of a ZnO single crystal.

FIG. 2 shows two spectra from 2 keV Helium backscattering from a ZnO single crystal. A 2 keV $He^+$ ion beam was used (Aono et al., 1992). In spectrum (b) (top) the sample surface was tilted by 68 degrees from the Helium beam. The Helium scattered from Zinc is well resolved but no signal from Oxygen is observed. By contrast when the beam impinges the surface at 0 degrees incidence (normal to the surface), the backscatter from Zinc is no longer well resolved in spectrum (a) (bottom) since a direct hit by the primary Helium onto the Zinc is blocked by a surface Oxygen. However Helium scatter from the surface Oxygen is not seen in either (a) nor (b), simply because the cross-section for Helium backscatter decreases significantly as a function of the atomic number (Z) of a surface element.

Figure 3A:
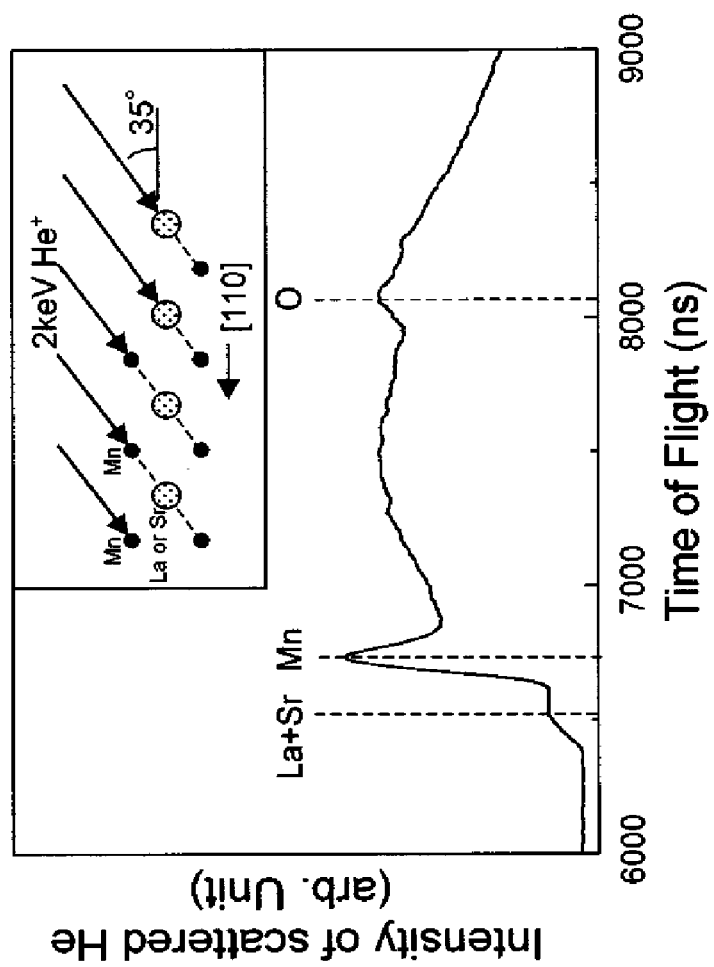
FIG. 3A shows CAICISS-TOF spectrum recorded at the incident angle of 35° along azimuth for the $La_{0.7}Sr_{0.3}MnO_3$ film surface.
Figure 3B:
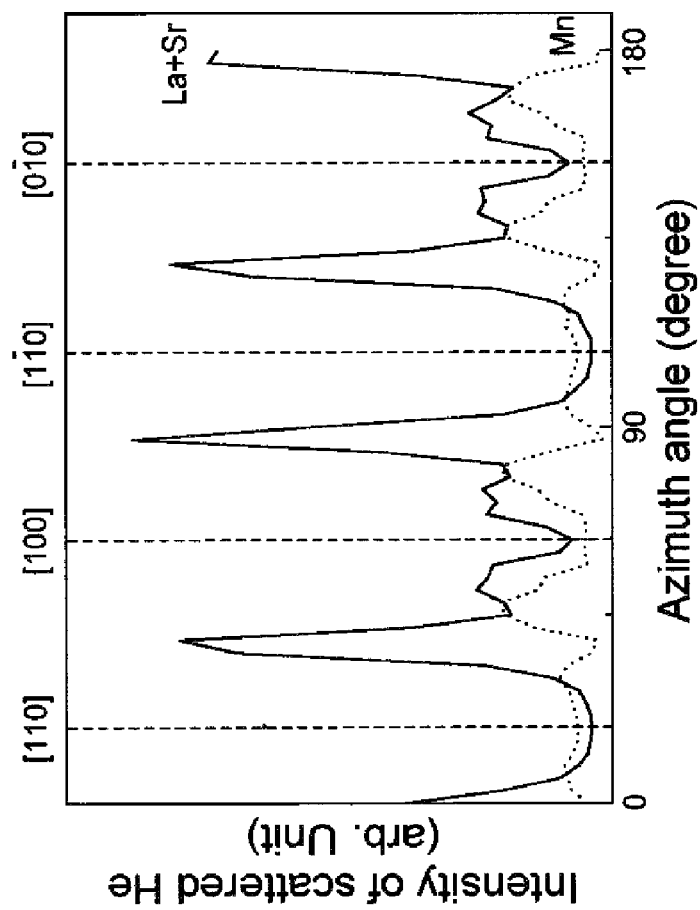
FIG. 3B shows the Azimuth angle dependence of (La+Sr) and Mn signal intensities at the incident angle of 35° for the $La_{0.7}Sr_{0.3}MnO_3$ film surface.

FIG. 3A shows the Helium Time-of-Flight backscatter spectra obtained with the beam incident at 55° (elevation above the surface plane is 35°) to examine the structure of the surface by the backscattered of Helium ions/neutrals (Ohnishi et al., 1998). As stated above, Lanthanum (La) and Strontium (Sr) cannot be resolved due to their similar masses which result in nearly equal Helium backscatter flight times. The dependence of the scattered Helium intensity on the azimuthal angle (angle by which the surface is rotated around its normal) is shown in FIG. 3B. The signal intensities can vary significantly depending on the azimuthal scattering angle, the scattering from heavy species like Lanthanum (La) or Strontium (Sr) versus lighter materials like Manganese and depending on the surface structure (where each element is shadowing and blocking its nearest neighbor at certain angles). The Azimuthal angle and/or elevation scanning (rotation and/or tilting) of the sample relative to the Helium beam incidence plane can be to provide information regarding local surface crystallography and these techniques yield local geometries which cannot be measured by more long-wavelength diffraction techniques such as electron or x-ray diffraction. The variance in backscattering intensities as a function of atomic number (Z) would be lower from this sample if a Neon ion beam were used since the overall variance of Neon backscatter cross-sections is less as a function of atomic number (Z); however, Neon cannot backscatter from any element lighter than itself which precludes any backscattering from first row elements such as Fluorine. The lighter elements are efficiently recoiled by the Neon towards the surface. The lighter elements then recoil backwards and/or sideways from their heavier nearest neighbors and the lighter elements arrive at the backscatter detector with keV type energies and flight times which are faster than the backscattered Neon. However, not much practical use has been made of this phenomenon other than to study the essential physics of the multiple atom collision sequences involved.

Figure 4:
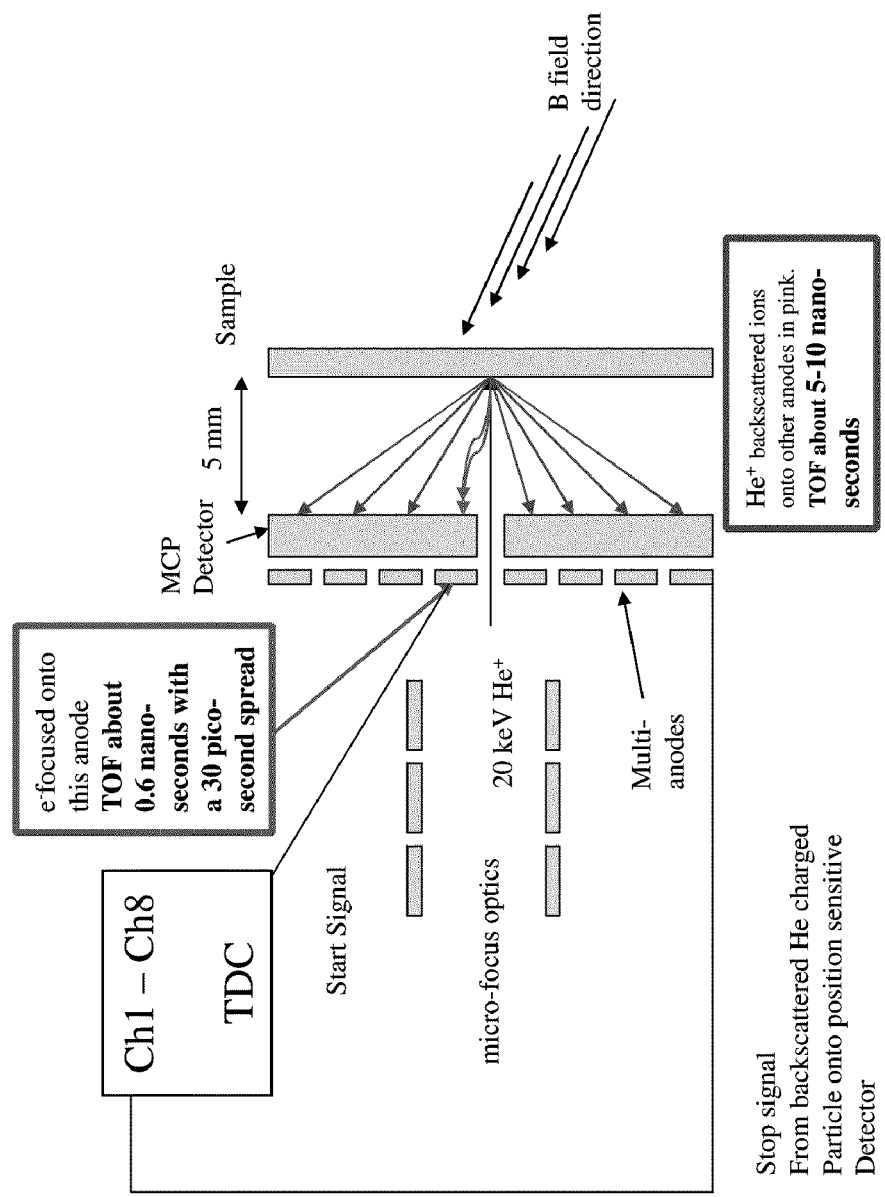
FIG. 4 shows the angle and time resolved particle detector.

One of the most general embodiments of the invention is seen in FIG. 4. Note the path-length scale difference (5 millimeters compared to 500 millimeters) and that the angle subtended by the detector will now be over 120 degrees compared with only a few degrees for the CAICISS technique. Longer flight paths are not needed in order to obtain accurate backscatter spectra provided that the time of arrival of the primary ion at the surface can be determined within a few hundred picoseconds or less. This aspect of the present invention has heretofore not been recognized or appreciated in the art. This high timing accuracy sensing of the ion arrival at the surface is accomplished by measuring the timing signal generated by secondary electrons (or VUV photons induced from the surface by particle collisions) which are generated when an ion strikes the surface are used to produces a start signal. Determining this signal allows picosecond timing resolution of any subsequent Time-of-Flight spectrum of any particles scattered or subsequently emitted from the surface. In addition to detecting backscattered primary ions with such a detector, the user may record multiple collision sequences involving several atomic collisions between primary particles and surface atoms which, in addition to producing backscattered primary particles, also liberate electrons photons, and sputter secondary ions as well as recoiled surface atoms with keV energies. Also an important coincident sequence involves multiple collisions which can liberate all light (as well as heavy elements) from the surface as recoils which can exit to the detector. The device described herein can be used to uniquely count the number of secondary electrons generated in the collision which allows recording secondary electron contrasts (to enhance image contrasts) from each ion collision.

The embodiment shown in FIG. 4, the micro-focused primary ions enter through a hole in a multichannel plate detector (MCP) with a multi-anode array (or other position sensitive detector) positioned behind the multichannel plates. The secondary electrons (or photons) produce a start signal which indicates that one microfocused primary ion (Helium in this figure) has hit the surface. A weak electric field (of between 0.5 volt/cm to 1 kvolt/cm between the sample and the detector) accelerates the secondary electrons from the sample to the detector and the flight times are on the order of 0.6 nanoseconds with a 300 picosecond spread (without magnetic field) and 30 picoseconds with the magnetic (B) field. In some embodiments, the magnetic field is not necessary since the highest timing resolution is not required. Some additional and/or alternate embodiments do not require the directing of the secondary electrons using the magnetic field to specific anode regions. Omission of the magnetic field certainly simplifies the construction and operation of the detector but decreases the likely capture of some of the secondary electrons. Both low and high timing resolution (without or with magnetic field) in this instrument can resolve elemental backscatters with resolutions comparable to or exceeding that seen in FIG. 2 and FIG. 3 from the much larger conventional instrument.

TABLE 1**

| Element | 163.3° scattering angle | | 122° scattering angle | |
|---|---|---|---|---|
| Scattered from in the surface (amu) | $E_{backscattered\ Helium}$ (keV) | TOF (nanoseconds) | $E_{backscattered\ Helium}$ (keV) | TOF (nanosecond) |
| Carbon (12) | 5142.9 | 10.4797 | 6889.7 | 16.3567 |
| Arsenic (75) | 16227.3 | 5.8997 | 16985.6 | 10.4173 |
| Indium (115) | 17452.4 | 5.6889 | 17979.9 | 10.1252 |
| Gold (197) | 18471.3 | 5.5298 | 18795.1 | 9.9032 |

**20 keV He$^+$ micro-focused onto a sample will backscatter with the above Energies and TOF into Detector 5 millimeters away.

TABLE 2++

| Element Scattered from in the surface (amu) | 163.3° scattering angle | | 122° scattering angle | |
|---|---|---|---|---|
| | $E_{backscattered}$ (keV) | TOF (µsec) | $E_{backscattered}$ (keV) | TOF (µsec) |
| Carbon (12) | 1452.0 | 0.0441017 | FORBIDDEN | — |
| Arsenic (75) | 6856.3 | 0.0202953 | 8645.0 | 0.0326511 |
| Indium (115) | 10050.4 | 0.0167629 | 11674.8 | 0.0280968 |
| Gold (197) | 13420.8 | 0.0145062 | 14641.8 | 0.0250891 |

++20 keV Ne$^+$ micro-focused onto a sample will backscatter with the following Energies and TIME-OF-FLIGHT into Detector 5 millimeters away Table 1 and Table 2 give some calculated times of flight for backscattering of Helium (or Neon) from chosen examples of heavy and light elements. For insulating materials the primary beam quickly charges the surface which can deflect the position and focus of the primary beam (as well as any secondary electrons liberated). This problem may be minimized or eliminated by the application of a low energy flood of electrons which neutralize the charged surface. In some embodiments this neutralization process can be controlled and used in conjunction with the detector since the number of electrons is being accurately measured for each ion impingement. This allows for the surface to be maintained electrically neutral by replenishing electrons from a separate electron source the same number of secondary electrons which have been ejected from the surface during the ion collision. For imaging metals and semiconductors, it is usually not necessary to us an electron flood, as surface charging is not typically a problem for such materials.

The present invention provides a device that allows the use of a continuous micro-focused ion beam. The spot size and low beam currents of micro-focused ion beams are well suited to ensure that the average time between primary particle impacts on the surface is more than several hundred nanoseconds, so there is no need to pulse the beam and subsequently ruin the spot size of the micro-focusing since all the time of flight particles scatter and recoil.

Angularly Resolved Backscattering

The micro-focused ions enter through a hole in a MCP with a multi-anode array (or other position sensitive detector) positioned behind the multichannel plates to the sample surface. A weak electric field (of a few hundred volt/cm between the sample and the detector) accelerates the secondary electrons from the sample to the detector and the flight times are on the order of around 2 nanoseconds with a 300 picosecond spread (without magnetic field) The secondary electrons (or photons) produce a start signal which is used as a time marker to indicate that one microfocused primary ion (for example, Helium) has hit the surface. The beam fluence is preferably adjusted so, that on average, only one ion hits within a 1 microsecond window. The average number of ions per unit time arriving at the surface may be calculated using industry standard techniques. For example, if a femtoampere primary ion beam current is being used, then the average number of ions in one microsecond or less is calculated by dividing the number of ions in a femtoampere by one microsecond. In another example, the instrument is tuned to 100 femtoamperes. One hundred femtoamperes is equal to $100 \times 10^{-15}$ coulombs/second and the charge on each ion is $1.6 \times 10^{-19}$ coulomb/ion. By dividing the charge per ion by the charge per second, it is determined that the average number of microseconds per ion is 1.6. These examples are not limiting, the skilled artisan will readily recognize alternative methods for calculating the average number of ions per unit time arriving at the surface without deviating from the spirit and scope of the present invention. Thus, the probability that a second primary ion will hit within the backscatter time of flight of the first ion (e.g. 50 nanoseconds) is extremely small. The small percentage of ions which do overlap in a time within the backscattering time frame can be ignored since these will on average contribute a small random background which will be distributed over all times and angles.

Addition of Focusing Magnetic Field

A weak electric field (of between 0.5 volt/cm to 1 kvolt/cm between the sample and the detector) accelerates the secondary electrons from the sample to the detector and the flight times are on the order of 0.6 nanoseconds with a 300 picosecond spread (without magnetic field) and 30 picoseconds with the magnetic (B) field. In some embodiments, the magnetic field is not necessary since the highest timing resolution is not required. Some additional and/or alternate embodiments do not require the directing of the secondary electrons using the magnetic field to specific anode regions. Omission of the magnetic field certainly simplifies the construction and operation of the detector but decreases the likely capture of some of the secondary electrons. Additionally, the lack of magnetic field reduces the beam damage necessary to obtain an ion induced secondary image. More importantly the magnetic field allows the electron yield to be determined for each and every collision. By correlating the co-incidence of the backscatter with the electron yields, a differential yield of secondary electrons can be shown to originate in regions of the crystallite which contains atoms that were identified by the backscatter experiment. This type correlation among other coincident particles is also possible. It is possible to detect and identify the recoiled surface elements because the recoiled surface elements are in co-incidence with the electrons. Both low and high timing resolution (without or with magnetic field) can resolve elemental backscatters with resolutions comparable to or exceeding those from the larger conventional instrument as seen in FIG. 2 and FIG. 3. Table 1 and Table 2 give some calculated times of flight for the backscattering of Helium (or Neon) from heavy and light elements.

The magnetic field and localization of all secondary electrons into one region allows a number of advantages: 1) sub 50 picosecond timing resolution of the impact time of the primary particle, 2) digital timing and counting of the number of electrons ejected in each collision by constructing multiple anodes behind the region of the MCP where the electrons are focused, or digital counting and timing of the number of electrons passing through an alternative second hole in the MCP so that electrons pass through to a multichannel dynode or multichannel "channeltron" type electron multiplier, 3) precisely measuring the time interval between successive primary ion arrivals which allows the use of Haddamard transforms for certain applications or for numerically excluding any false coincidences 4) determining the number of electrons which have been emitted which allows resupplying those numbers of electrons by a very precisely controlled electron flood constructed so that the electrons can be put back down the magnetic field path to neutralize exactly that area of an insulator surface which was interrogated (and charged) by the focused ion beam.

Thus, the angle and time resolved particle detector described in FIG. 4 is extremely versatile and can be used in conjunction with a focused keV energy ion beam to measure coincidences generated when each ion from the focused ion beam sequentially strikes a surface. The primary ion beam fluence in a microfocused beam is inherently small (1 picoampere or less) so this ensures that, on average, only one primary ion hits the surface at any one time within a time interval of several hundred nanoseconds. Many processes happen and evolve simultaneously (within a 50 nanosecond time period after the primary ion strikes the surface as can be seen in Table 1) during the collision of each ion with the surface. All of these processes liberate energetic particles whose energy and intensity can give detailed information about the atomic composition of the surface as well as the electronic and geometric structure resulting from the arrangement of these atoms on the surface or within the near surface region.

Elemental information can be gleaned from the arrival time data and angular trajectories of electrons, photons, recoiled atoms and backscattered atoms and ions arriving in coincidence at the Time-of-Flight detector. As the low currents are being microfocused e.g. roughly 150 femtoamps, a high data rate multi-anode or multi-positions sensitive detector allows the beam to run continuously while acquiring time resolved data at high resolution during a 100 nanoseconds time period and with high angular resolution over a very large range of backscatter angles. For example, the acceptance cone centered on 180 degree backscatter with 120 angle is defined by a 50 millimeters MCP plate placed 5 millimeters away from the sample. At these low operating currents, there would be one Helium ion striking a surface roughly every microsecond. Most electrons will travel the distance to the detector in less the 2 nanoseconds which is much less than the subsequent travel times of the backscattered ions—as seen in the Table 1 and Table 2, 20 keV He$^+$ or Ne$^+$ ions backscatter from different elements with times of flights over a 5 millimeters path length ranging from 5 nanoseconds from the heaviest elements to 10 nanoseconds for the lighter elements. The Helium backscatter times are concentrated in a relatively narrow time range because of the large difference in mass between the incident ion and the target. By contrast, Neon backscattering occurs over a much wider time range in the flight times (see Table 2).

Scattering cross sections for Helium can increase by more than an order of magnitude as the atomic mass (Z) increases from light to heavy elements. In contrast the scattering cross-section for Neon varies by roughly a factor of 3 over all elements which are heavier than Neon. The cross sections for Neon are also an order of magnitude larger than the cross sections for Helium.

Each primary ion will hit the analyte surface and subsequently create secondary electrons as they either penetrate into the surface or backscatter into the detector. The corresponding energy and angle of the backscattered ion or neutral will give information which will correspond to the surface atom present. Backscattering is normally done with a low atomic number primary ion which has a small mass like Helium. Helium will backscatter from all elements present in the surface except Hydrogen. To generate primary ion arrival timing signals, the secondary electron signal generated from the Helium ion hitting the substrate surface will be used to start a time-to-digital converter (for example, an eight channel time-to-digital converter). The travel times for the electrons can be seen below in Table 3.

mation required. FIG. 5C shows an alternate embodiment wherein an electrostatic lens is used to extract electrons from the point of impact and to accelerate the electrons quickly towards a second MCP multianode position sensitive detector. The second MCP multianode position sensitive detector is used to exclusively record secondary electrons from each Helium impact. By making the distance between the entrance of the lens to within a few hundred microns to a few millimeters from the point of Helium impact and using a positive bias of a few volts to a hundred volts, the timing resolution of the electrons is well under 100 picoseconds. An optional magnetic field along the axis of this lens can be applied by a solenoid. The solenoid is internal to the lens and its magnetic field can be magnetically shielded. The magnetic shielding does not allow the magnetic field of the solenoid to penetrate outside the lens. An additional and/or alternate embodiment is shown in FIG. 5D. FIG. 5D shows an embodiment in which no magnetic field is used and the electron trajectories are allowed to impact the entire position sensitive backscatter detector surface. The entire position sensitive backscatter detector surface is understood to have a transparent electrically biasable grid on its front. Trajectories of electrons with energies of between 2 and 10 eV and with backscatter angles of between 100 and 160 degrees are illustrated when an

TABLE 3[‡]

| Secondary Electron Energy (eV) | Average TOF (nano-seconds) | | Δ TOF (pico-seconds) | |
| --- | --- | --- | --- | --- |
| | (160°-100°) towards magnetic field | (160°-100°) away from magnetic field | (160°-100°) towards magnetic field | (160°-100°) away from magnetic field |
| 2 | 0.6868 | 0.7018 | 15.6 | 29.1 |
| 4 | 0.6764 | 0.6977 | 21.7 | 40.9 |
| 6 | 0.6685 | 0.6946 | 26.2 | 49.5 |
| 8 | 0.6619 | 0.6920 | 29.9 | 56.9 |
| 10 | 0.6561 | 0.6897 | 33.0 | 63.2 |

[‡]Secondary electrons with these energies are scattered from the surface with these flight times. Note with 500 gauss field and 1000 V bias on the detector surface, gives an average TOF about 0.6826 nano-seconds and a FWHM of about 32 pico-seconds.

The secondary electrons will come off the surface at a variety of angles and energies (typically less than 10 eV), whether it is a biological sample like those used in MALDI or one of interest in the semiconducting field. A magnetic field can be used (as shown in FIG. 5B) to align the electrons and give them similar flight times to one specific region and area of the detector. This area or anode region will be used to generate the start signal as the primary ion strikes the sample so that the time of flight of the ions/neutrals may be measured when they strike the detector. The electrons are very easy to confine and direct along the magnetic fields compared to the magnetic fields needed to move the same ions. Using the device and methods described herein, one may direct the electrons to one region of the anode structure of the detector. It is possible to have an annular anode structure for detecting the electrons in more than one region.

Figure 5A:
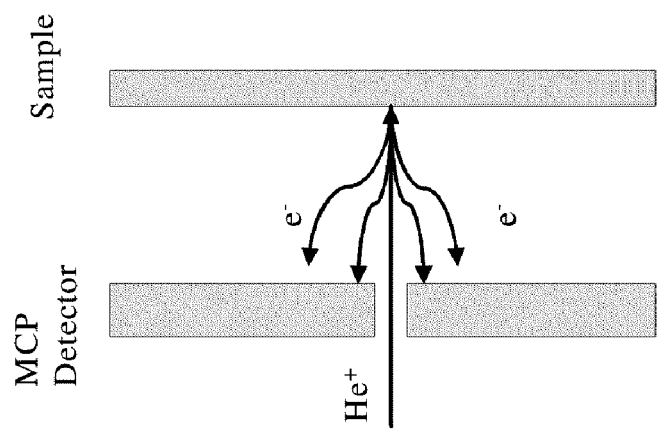
FIG. 5A shows an example of the secondary electrons scattering from the surface after collision with no magnetic field and only in the presence of an electric field between sample and detector and slight bias within the clearance hole in the detector.
Figure 5B:
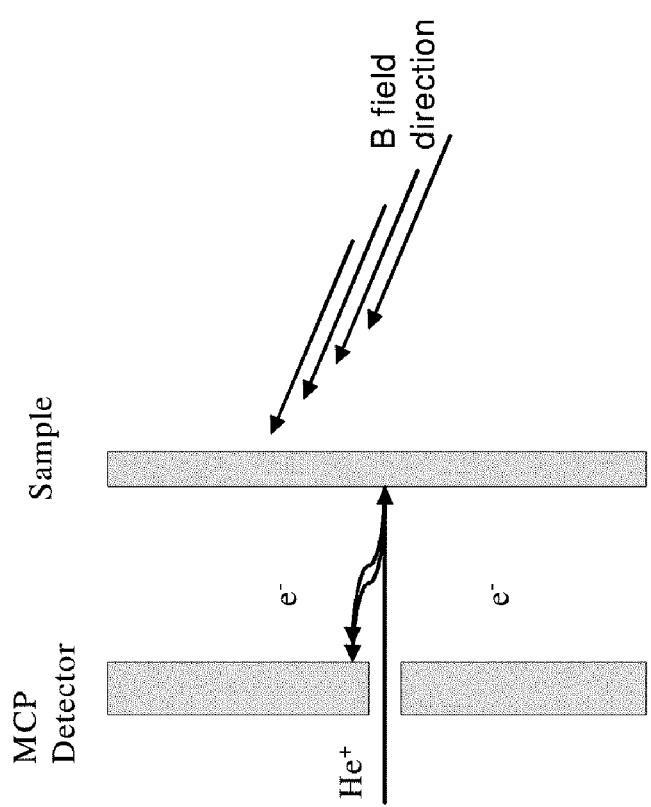
FIG. 5B shows an example of the secondary electrons scattering from the surface after collision after a magnetic field is applied.
Figure 5C:
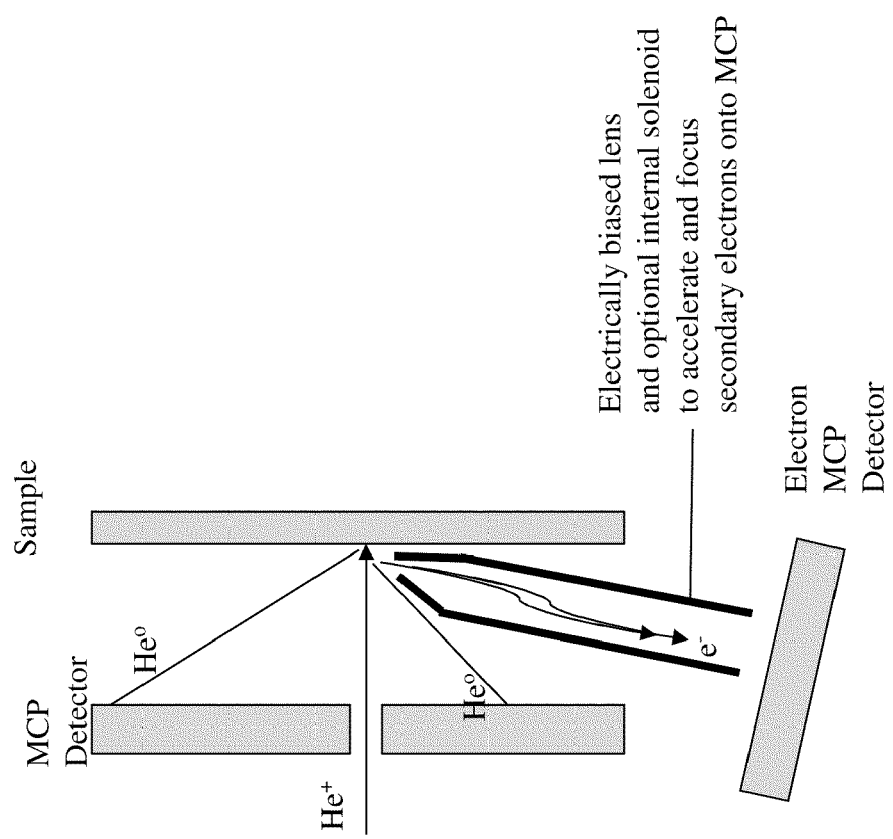
FIG. 5C shows an embodiment wherein an electrostatic lens is used to extract electrons from the point of impact and to accelerate the electrons quickly towards a second MCP multianode position sensitive detector.
Figure 5D:
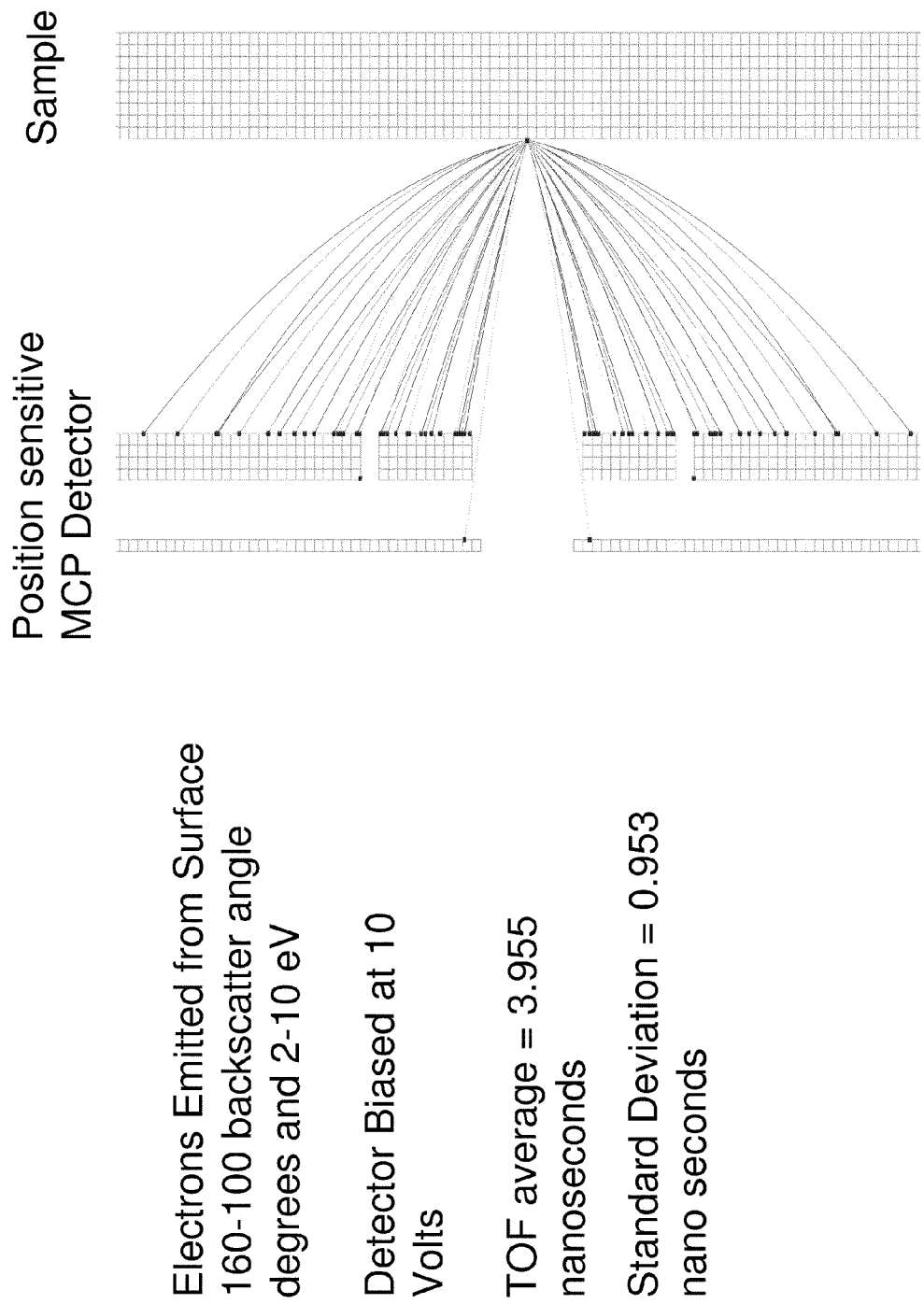
FIG. 5D shows an embodiment in which no magnetic field is used and the electron trajectories are allowed to impact the entire position sensitive backscatter detector surface.

FIG. 5A shows an example of the secondary electrons scattering from the surface after collision in absence of a magnetic field (only an electric field between sample and detector and slight bias within the clearance hole in the detector). FIG. 5B shows an example of the secondary electrons scattering from the surface after collision in presence of a magnetic field. After a magnetic field is applied, electrons align along the field direction, including those electrons which were initially headed away from the magnetic field direction. Timing the electrons in a mode with or without the applied magnetic field are both useful depending on the inforelectrical bias of 10 volts has been applied between the surface and the grid face of the MCP position sensitive detector. A large number of electrons with different energies and angles are focused onto the grid. A bias between the front plate of the MCP and the electrically biased grid can further accelerate the electrons to around 200 eV or more. This acceleration enhances the detection efficiency within the MCP detector. The overall timing spread of electrons averaged over the entire face of the position sensitive detector is under one nanosecond. Additional timing accuracy can be obtained by recording the position of impact of the electrons. The electrons with trajectories to the outer rim have much longer times of flight and higher energies than the electrons with trajectories near the middle of the backscatter detector. Only certain angles and energies will be just right for the electrons to land on one particular small area of the detector. Thus, knowing the position of impact of the electrons defines a distance from the point of impact of the Helium ion which produced them. Only a few of the many trajectories can impact this position uniquely. The flight time will increase as the electron's point of impact moves from the center to the outer rim of the detector and the time spread of different angles and energies of the electrons arriving at a specific location will be small. Thus a correction can be applied empirically to compensate for the known distance traveled which allows for the time of arrival of the Helium primary ion at the surface to be determined. This embodiment has another advantage that multiple electrons are spread over different areas of the position sensitive detector. Multianode arrays allow simultaneous detection of many nearly simultaneously arriving electrons. This allows for the number and positions of each of the multiple electrons released by the impinging Helium primary ion to be recorded and correlated with an individual Helium primary ion's impact on the surface. Another exemplary use is that the integral energy distribution of the emitted electrons can be determined by scanning the electrostatic potential between the sample and the grid in front of the backscatter position sensitive detector. As the electrostatic potential is incrementally increased between the ranges of about 1 eV up to about 200 eV the possible combinations of energy and angles of the electrons which can hit at any one spot change. By acquiring the position information of the electrons as a function of this bias the integral energy of the secondary electrons produced by $He^+$ or $He^{+2}$ neutralization is obtained with enough angular and energy resolution to be useful in determining the band structure of the solid. Electrons are released in a well known surface Auger process in which one electron from the valence band of the solid falls into the hole of the approaching He ion. The remaining potential energy liberated by this neutralization appears in the kinetic energy of a second electron from the valence band which is liberated into the vacuum. The measurement of the angle and energy of these Auger electrons gives information about the band structure of the solid.

Surface Crystallography of Nanocrystals.

By using time of flight backscattering, the capability of the microfocused ion beam is enhanced not only for spatially resolved elemental analysis but for characterizing individual crystallites whose dimensions are equal to or greater than the focal size of the beam.

Multiple Collision Sequences for Surface Recoil and Backscatter Coincidences.

The energy and time-of-flight of the backscatter energy of Neon after it collides with a lighter surface bound element (Hydrogen (H), Deuterium (D), Lithium (Li), Oxygen (O) etc.) and then continues on toward the surface along with the now recoiled and energized surface bound atom can be computed for specific multiple collision sequences. For example, if Hydrogen (H) were bound to Tungsten (W) as a hydride when the Neon collides with complex the $H^-$ backscatters from the $W^+$ while the Neon momentarily continues onward until it too hits the same $W^+$ to which the $H^-$ was bound. Thereby, two particles are coincidentally backscattered into the detector which contain information about the Hydrogen and the Tungsten. The scatter time of the Neon backscatter energy will be much less than the original energy (10 keV). This is because the original energy is first reduced by a collision with a light element and then further reduced by its subsequent collision with the underlying heavy element from which it then backscatters. These multiple scattering sequences broaden the backscatter distribution that is actually measured such as in FIG. 2 and FIG. 3. By detecting the angle and the energy of the co-incident Neon and Hydrogen, the specific sequences which serve to broaden the backscatter spectrum can be unraveled and additional useful information can be obtained.

Because the Hydrogen and the Neon scatter have been measured in co-incidence only, there is one unique combination of recoil elements. The unique combination of recoil elements include: Hydrogen and Neon, backscatter time (Neon from W) and the surface atom (W) to which H was bound and from which it recoiled and Neon backscattered. The flight time and recoil angle of the H can be measured and the flight time and recoil angle can be inferred by assuming the collision sequences are similar to those tabulated in Table 3. For simplicity, the energies and flight times for 180 degree light element recoil sequences and coincident Neon backscatter sequences are calculated and tabulated. These calculations can be generalized for all angles measured by the large range of backscatter angles between 130 and 180 degrees subtended by the detector.

Typically, these backscatter sequences are easily measured since the backscatter sequences are in coincidence with the electron, the angle and the energy of only two additional particles that are measured: one which is the surface recoiled light element and the other is the backscattered Neon after it has first lost energy to the particular light element and then has recoiled from the underlying heavy element. In general, much more intensity and many more coincidences are seen between the surface recoil (SR) light atom and the Neon at smaller scattering angles where the SR light atom would travel in one direction at one scatter angle with a certain energy and the Neon would travel in another direction with a particular scatter angle and energy as required by the conservation of kinetic energy and momentum (billiard ball kinematics). The coincidences may be uniquely measured and correlated with the same primary particle collision since only three particles are being detecting in co-incidence electrons (identified by their magnetic field focusing into one small area of the detector), surface recoils (SR) (into one position on the PSD detector for any one primary ion collision) and the primary multiple scattered Neon (into an opposite position and a different arrival time compared to the SR). The measurement is relatively simple and fast PSD because there is plenty of time (hundreds of nanoseconds or more on average) before the arrival of the next primary particle. This is because the two angles and energies predict a certain sequence for any two pairs of surface atoms hit by the Neon. From roughly a few thousand of these coincidence pairs, one can deduce which element is adjacent to another element and even deduce something about their geometric positions and bond lengths on the surface. This includes especially hydrogen, which can be visualized in no other way. The use of $Ne^{+2}$ (or higher m/z charge states) can also be beneficial. Prior to collision as Neon approaches the surface, $Ne^{+2}$ liberates Auger electrons from the valence band of the solid. The energy and angle of the Auger electrons can be measured because they are in co-incidence. Furthermore, the collision of energetic Neon with light elements causes VUV emission from the light elements almost exclusively. These VUV photons can also be detected by the detector almost instantly and the resulting signal can form anywhere on the detector. The photons can be distinguished from the coincident electrons by two features: 1) the photons appear at a time slightly shorter than the arrival time of the electrons at the detector (since the electrons are traveling only at around 10% of light speed) and 2) from the location at which they are recorded by the position sensitive detector since the faster photons are diffuse while the electrons are localized into their detector area by the magnetic field.

The fitting of the co-incidence data to sequential calculations is made much easier and more reliable if in-situ measurements are made to determine what elements are on the surface. The in-situ measurement may be done, for example, by MSRI (Mass Spectrometry of Recoiled ions) XPS and/or AES. This can be done in real time by constructing a CMA type analyzer in which the microfocused beam and co-axial backscatter detector are introduced co-axially through an axially symmetric curved energy analyzer which is itself equipped with a position sensitive detector. With such an analyzer, the energy and time of flight of any ionized particle which was recoiled or scattered from the surface at a scattering angle less than 120 degrees is measured. These ionized particles are those leaving the surface at a very grazing elevation which would fly under the outer edge of the positions sensitive backscatter detector. While of course the MSRI does not give elemental concentrations, it does tell very effectively if an element (or an isotope) is or is not present. From the MSRI intensities it is possible to deduce the rough concentration of the elements present. Measurements are made using MSRI. MSRI is used because of the surface type and of the likely probability of neutralizing the types of ion exiting such a surface. Specific elements known to be on the surface reduces the number of possible collision partners that must be used to simulate the measured backscatter distributions.

The elemental concentration may be determined very accurately for most elements by intermittently firing a VUV laser across the surface in order to sample the secondary neutrals. The secondary neutrals have been sputtered by a number of previous Neon collisions and are slowly moving away from the surface. After each laser pulse, a linear time of flight analysis is performed or the CMA may be used to obtain the elemental post-ionized mass spectrum.

In another embodiment combining coincident backscatter, MSRI, and post-ionization involves subtending a narrow angular range selected around a nominal scattering angle. The nominal scattering angle has an elevation angle that allows the surface recoiled ions to clear the surface of the sample. The nominal scattering angle is less than 120 degrees so that the surface recoiled ions do not collide with the backscatter detector. The recoiled ions are allowed to enter along the longitudinal axis of a gridded capacitor which is intermittently pulsed by high voltage to orthogonally deflect the ions within the capacitor onto a time of flight detector (orthogonal Time-Of-Flight mass spectrometry).

Step Edge Densities and Comparison with Ex-Situ LEED RHEED and XRay Diffraction.

The microfocused beam incidence can be inclined to a grazing incidence so that shadow cones prohibit any primary backscattering from an atom within a smooth single crystalline surface. Thus, only the backscatter signal to arrive at the detector will be free from defects (i.e. step edges or kinks).

Imaging of Biological Surfaces During NP Matrix Implantation.

This device will solve a longstanding dichotomy encountered when coupling surface imaging with surface analysis—the ion beam must be microfocused to submicron (and even nanometer) focal spots in order to generate information from the smallest area possible; however, the ion beam must be pulsed with the shortest time possible if surface elemental and molecular identification is to be obtained by time of flight analysis of the secondary particles ejected from within the microfocused area. Electrically deflecting the primary ion beam to produce sub-nanosecond time packets of ions not only causes severe defocusing of the beam spot size but increases (by more than 100) the time required to obtain spatial images.

Figure 6A:
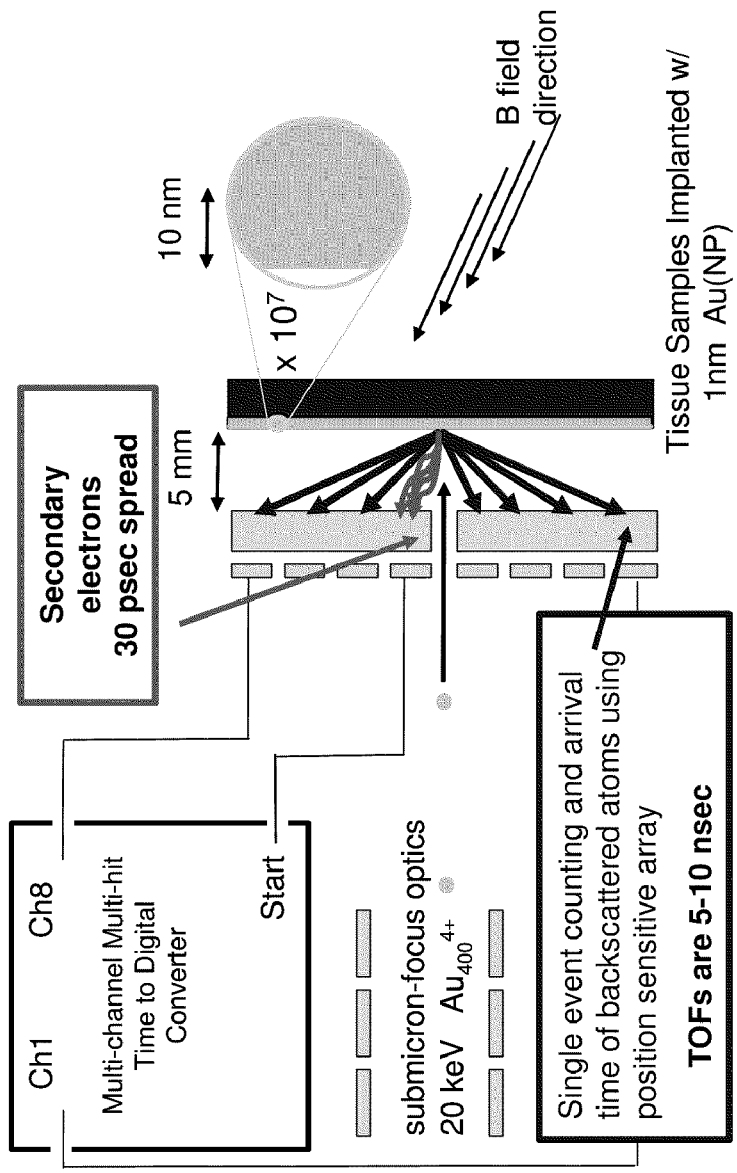
FIG. 6A shows the Co-incidence Detector for Secondary Electron and Backscattered Particles when implanting microfocused clusters into biotissues.
Figure 6B:
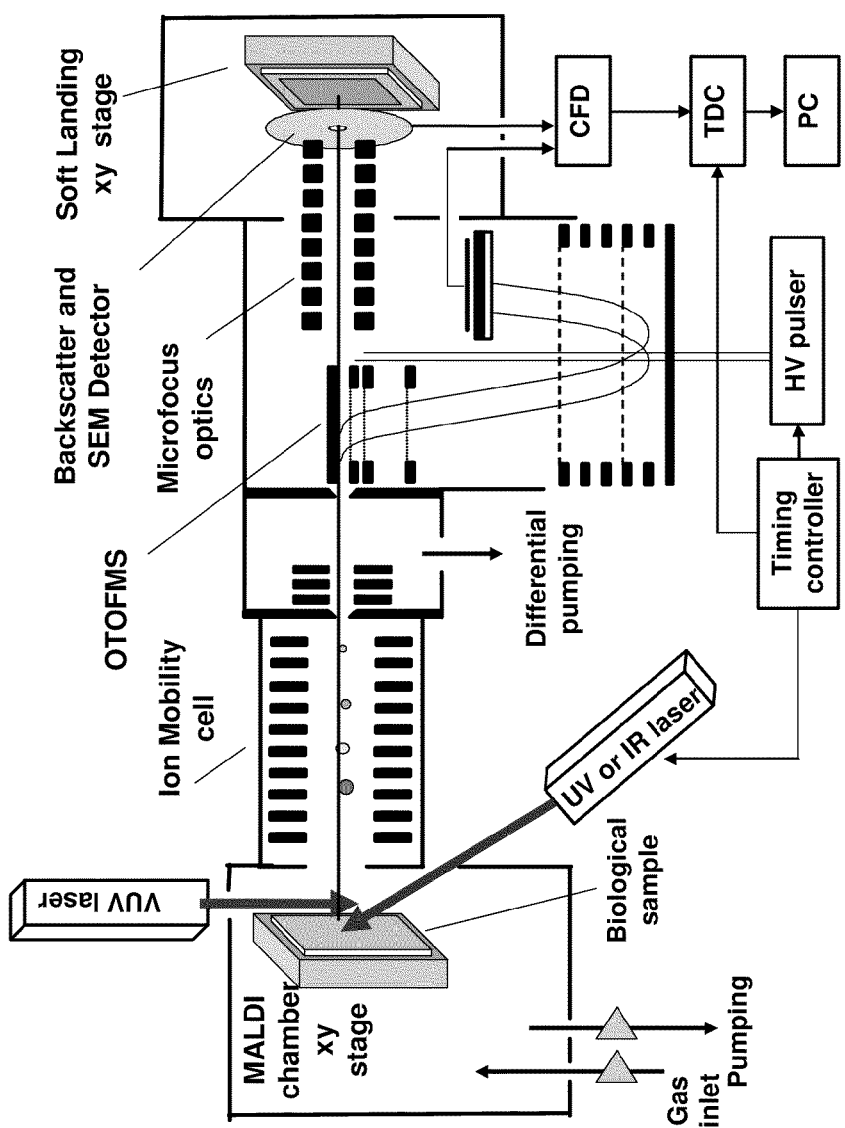
FIG. 6B shows a schematic of the UV or IR/VUV MALDI-Ion Mobility-oTOFMS.

FIG. 6 shows a microfocused ion beam with a detector for accurately measuring the arrival time of individual microfocused particles at the surface. This is accomplished both by counting each secondary electron and by also measuring its arrival flight time after the primary particle's collision with the surface. The number of electrons provide a means for obtaining the imaging contrast and the arrival time distribution provides a means for obtaining a very accurate start time for any subsequent time of flight measurement of the slower backscattered or secondary ion particles also liberated during the primary ion collision. The average time between individual ion arrivals in a 100 femto-ampere micro-focused beam is 2 microseconds. There is only a small probability that more than one primary particle impacts the surface during the 50 nanoseconds fight times of the backscattered particles. Therefore, the electrons and the backscattered particles from the surface can all be timed relative to the individual arrival of primary particles.

The detector can be used with large particles such as the 1 nm AuNP illustrated in FIG. 6. This is a very useful application of the present invention since the instrument is then ideal for implanting nanoparticulates into bio-tissue. The implanted nanoparticles may serve as highly efficient matrices for laser desorption of biomolecules for imaging analysis. Thus the instrument is capable of implanting nanoparticulates (and simultaneously obtaining the SEM picture during implantation) into a biological surface mounted on the soft landing stage. After implantation, the sample is then transferred from the softlanding chamber to the MALDI imaging chamber (left side in FIG. 2) for imaging. Thus, the combined instrument can perform matrix implantation and subsequent imaging analysis of samples within one piece of hardware.

In the mechanical design, the detector is modified to be used with a micro-focused ion beam. The micro-focused ion beam provides the user a small spot size beam able to limit the area of interact with the surface. The implementation of a fixed magnetic field at an inclined angle to the incident ions allows the user to focus the emitted electrons onto one region of the detector by adjusting the magnetic field strength.

Additional embodiments of this invention derive from its capability of accurate measurement of the exact moment of impact of the individual primary ions on a surface. This time of impact can then be used as a start signal, not only for measuring the backscattered primary particle energy distribution by time of flight, but also by using this time as the start of other time of flight analysis into other spectrometers which are attached to view line of sight particles emerging from the area between the positions sensitive detector and the sample. For example recoiled ions and elements can emerge with moderate energies and scattering angles which graze along the surface. This allows the particles to move away from the sample but miss the backscatter detector as they shoot the gap. The time of flight of these ions or neutrals relative to the time of He impact can, however, be measured by another position sensitive detector or detectors which have a line of sight view the open region between the sample and the backscatter detector. The plane of the MCPS in this line of sight detector is perpendicular to the plane of the surface and is located some few cm away from the optical axis of the ion beam. The time of arrival of these surface recoiled particles can be measured relative to the moment the individual He has been determined to strike the surface and with the known distance from the point of impact to this line of sight recoil detector the energies of surface recoil peaks can be calculated and compared to the measured distributions as described in detail in prior art. If the ion beam is tilted away from this line of sight detector then more and more of the forward scatter and recoil angles open up to the line of sight detector. Another embodiment would combine the line of sight detector with a reflectron detector as has also been shown in the prior art (Hammond).

This combination allows the ionized portion of the recoiled particles to be focused into to a reflectron time of flight mass spectrometer where their mass/charge of these ionized surface elements can be determine. This well established technique is call mass spectrometry of recoiled ions (MSRI). The neutral recoiled particles can pass through a hole in the end of the reflector to be detected by a line of sight detector. An alternative to the reflector mass spectrometer for this application is an orthogonal time of flight mass spectrometer (oTOFMS) which may be a linear or a reflectron type and whose operation is well known to skilled artisans. In this type of oTOFMS a set of gridded parallel plate electrodes forms a high voltage pulsed extraction capacitor assembly. The mass of the recoiled ions from the sample can be measured as follows: 1) the gridded capacitor is interposed between the sample and the external recoil detector. 2) The high voltage pulsed extraction capacitor assembly is oriented so that the recoiled ions from the surface traverse the capacitor assembly in a nearly parallel beam and in a direction nearly parallel to each extractor plate of the high voltage pulsed extraction capacitor assembly. 3) At measured times relative to the He impact time on the surface, a high voltage pulse is applied to the gridded extractor plates within the high voltage pulsed extraction capacitor assembly to give the ions a velocity component normal to the gridded capacitor plates. The ions are thus accelerated and pass through gridded capacitor plates and exit the high voltage pulsed extraction capacitor assembly in sideways direction toward a detector positioned facing the orthogonal plates with its face parallel to the high voltage pulsed extraction capacitor assembly. 4) The m/z of any ions i determined by timing their arrival at the linear detector relative to the time at which the a high voltage pulse is applied to the high voltage pulsed extraction capacitor assembly (this experiment can also be done where a reflector mass spectrometer is substituted in place of the linear detector). Each mass spectrum so acquired is time tagged in the data stream so that each mass spectrum from each high voltage orthogonal extraction pulse records the presence of each recoiled ion measured at a specific distance away from the point of He impact on the surface and at a specific time after the impact as defined by when the high voltage orthogonal extraction pulse is applied. Thus it is possible to reconstruct from these data the velocity of each recoiled ion by plotting the mass as a function of the time after the initial primary He impact occurs at which the high voltage extractor pulse was applied to generate the mass spectrum. Since the distance from the point of He impact to the high voltage pulse extractor is known, the velocity and hence the energy distribution of each of the recoiled ions can be constructed. Moreover, it is possible to time a vacuum ultraviolet laser to photoionize many of the more predominant neutral recoiled elements on the periodic table which are sputtered or recoiled from the surface by the primary ion. This experiment can be performed either in the traditional MSRI analyzer or in the above described oTOFMS. Using the oTOFMS the laser can be fired just above the surface some few nanosecond after the He has been determined to have impacted the surface. This will photoionize energetic neutral recoils (more than 60% of the elements of the periodic table can be photoionized with 7.8 eV photons from a fluorine excimer laser) and the energy distributions and mass distributions of these photoionized neutrals would be determined as previously described. Another possibility is to randomly fire the laser as fast as possible through the orthogonal extraction capacitor structure to photoionize any element which has been recoiled from the surface and is present in the extractor plates during the laser pulse. This measurement does not explicitly require the use of the primary He impact timing and the mass spectra are thus correlated directly to the position of the He beam on the surface at the time of the laser firing. Another possibility is to use a continuous source of photons from a very bright continuous VUV photon source focused in between the gridded capacitor plates of the high voltage pulsed extraction capacitor assembly and to apply high voltage extraction pulses to the oTOFMS as rapidly as possible. The mass spectra of the photoionized neutrals from this method may then can be correlated with the impact time of the individual primary ions as determined with the backscatter detector or the spectrum simply be correlated only with the impact position of the microfocused beam.

Another possible embodiment uses the high accuracy timing of the primary ion impact to start the timing in many different types of time of flight secondary ion mass spectrometers and is a perfect way to record negative ions signals in the commercial TRIFT spectrometer.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for analyzing a sample comprising:
   generating a continuous micro-focused beam of primary ions;
   directing the micro-focused beam of ions through an aperture in a position sensitive detector to a sample surface thereby creating a secondary species and backscattered primary species; said position sensitive detector having a Multi-channel plate and a multi-anode array, wherein said secondary species is selected from the group consisting of electrons, photons, recoiled atoms, backscattered atoms backscattered ions and any combination thereof, and wherein said backscattered primary species have a backscattering angle between 90 to 180 degrees with respect to the primary ion beam incidence;
   adjusting the micro-focused ion beam fluence such that about only one ion hits the sample surface within a 1 microsecond period;
   accelerating the secondary from the sample to the detector by applying an electric field between the sample and the detector;
   detecting the arrival time and angular trajectories of said backscattered primary species and said secondary species; wherein the secondary species is selected from the group consisting of electrons and/or photons arriving in coincidence at the time-of-flight detector;
   measuring a first timing signal from a first subset of secondary species selected from the group consisting of electrons, photons and any combination thereof and deriving this primary ion impact time by the known energies of the electrons or velocity of the photons and the geometry of the detector;
   measuring a second timing signal wherein the signal is generated when a second subset of secondary species strikes the detector, wherein said second subset of secondary species is selected from the group consisting of recoiled atoms, backscattered atoms, backscattered ions and any combination thereof;

calculating the times of flight for the secondary species and the backscattering primary species using a linear time of flight analysis and the measured position of the secondary species impact.

2. The method of claim 1, further comprising applying a magnetic field to direct said flow of secondary species.

3. The method of claim 1, wherein the overall surface composition is measured with a technique selected from the group consisting of MSRI, XPS, AES or any combination thereof and compared to a backscattering spectra.

4. The method of claim 3, wherein the generated micro-focused ion beam is selected from the group consisting of Helium, Neon, Indium, Gold, Gold/Silicon clusters, Gold/Germanium Clusters and any combination thereof.

5. A method for analyzing a sample comprising
generating a continuous micro-focused beam of primary ions;
directing the micro-focused beam of ions through an aperture in a position sensitive detector to a sample surface thereby creating a secondary species and backscattered primary species; said position sensitive detector having a Multi-channel plate and a multi-anode array, wherein said secondary species is selected from the group consisting of electrons, photons, recoiled atoms, backscattered atoms backscattered ions and any combination thereof, and wherein said backscattered primary species have a backscattering angle between 90 to 180 degrees with respect to the primary ion beam incidence;
adjusting the micro-focused ion beam fluence such that about only one ion hits the sample surface within a 1 microsecond period;
accelerating the secondary from the sample to the detector by applying an electric field between the sample and the detector;
intermittently firing a VUV laser across the surface in order to sample said secondary species;
detecting the arrival time and angular trajectories of said backscattered primary species and said secondary species; wherein the secondary species is selected from the group consisting of electrons and/or photons arriving in coincidence at the time-of-flight detector;
measuring a first timing signal from a first subset of secondary species selected from the group consisting of electrons, photons and any combination thereof and deriving this primary ion impact time by the known energies of the electrons or velocity of the photons and the geometry of the detector;
measuring a second timing signal wherein the signal is generated when a second subset of secondary species strikes the detector, wherein said second subset of secondary species is selected from the group consisting of recoiled atoms, backscattered atoms, backscattered ions and any combination thereof;
calculating the times of flight for the secondary species and the backscattering primary species using a linear time of flight analysis and the measured position of the secondary species impact.

6. The method of claim 5, further comprising applying a magnetic field to direct said flow of secondary species.

7. The method of claim 5, wherein the overall surface composition is measured with a technique selected from the group consisting of MSRI, XPS, AES or any combination thereof and compared to a backscattering spectra.

8. The method of claim 6, wherein the generated micro-focused ion beam is selected from the group consisting of Helium, Neon, Indium, Gold, Gold/Silicon clusters, Gold/Germanium Clusters and any combination thereof.

* * * * *